United States Patent [19]
Huse

[11] Patent Number: 5,955,358
[45] Date of Patent: Sep. 21, 1999

[54] OPTIMIZATION OF BINDING PROTEINS

[75] Inventor: William D. Huse, Del Mar, Calif.

[73] Assignee: Ixsys, Incorporated, San Diego

[21] Appl. No.: 08/386,197

[22] Filed: Feb. 9, 1995

Related U.S. Application Data

[63] Continuation of application No. 07/631,659, Dec. 20, 1990, abandoned.
[51] Int. Cl.$^6$ .......................... C12N 5/10; G01N 33/531; C07K 16/00
[52] U.S. Cl. .................. 435/328; 435/70.21; 435/172.3; 436/548; 530/387.3; 530/388.1; 935/15; 935/27; 935/31; 935/32; 935/66
[58] Field of Search .......................... 530/387.1, 388.1, 530/387.3; 435/69.6, 70.21, 172.3, 320.1, 240.27, 328; 436/547, 548; 935/15, 27, 31, 52, 66, 79; 424/130.1

[56] References Cited

U.S. PATENT DOCUMENTS

| | | | |
|---|---|---|---|
| 4,683,202 | 7/1987 | Mullis | 435/91 |
| 5,223,409 | 6/1993 | Ladner et al. | 435/69.7 |
| 5,270,163 | 12/1993 | Gold et al. | 435/6 |
| 5,403,484 | 4/1995 | Ladner et al. | 435/235.1 |
| 5,427,908 | 6/1995 | Dower et al. | 435/5 |
| 5,432,018 | 7/1995 | Dower et al. | 435/5 |

FOREIGN PATENT DOCUMENTS

| | | | |
|---|---|---|---|
| 0239400 | 9/1987 | European Pat. Off. | C12N 15/00 |
| 2188638 | 10/1987 | United Kingdom | C12N 15/00 |
| WO8806630 | 9/1989 | WIPO | C12P 21/00 |
| WO90/14443 | 11/1990 | WIPO . | |

OTHER PUBLICATIONS

Dauglierty et al Nucleic Acids Research 19(9):2471–2476 Polymerase Chain Reaction Facilitates . . . CDR Grafting. 1991.
Gavilondo–Cowley, Hybridoma, 9(5) : 407–417 (1990) "Specific Amplification of . . . Immunoglob. Var. Reg. Genes . . .".
Better et al Science 240: 1275 (1988).
Riechmann et al, Nature, vol. 332, pp. 323–327(1988) "Reshaping Antibodies for Therapy".
Queen et al, PNAS, vol. 86: 10029–10033 (1989) "A Humanized Antibody that Binds to the 1L–2 Receptor".
Traunecker et al, Immunology Today, vol. 10(1): 29–32 (1989) "Solublizing the T–cell Receptor–Problems in Solution".
Hodgson, Bio/technology, vol. 8: 1245–1247 (1990) "Protein Design : Rules, Empiricism, & Nature".
Cwirla et al., Peptides on phage: A vast library of peptides for identifying ligands, Proc. Natl. Acad. Sci. USA vol. 87:6378–6382 (1990).
Scott & Smith, Searching for Peptide Ligands with an Epitope Library Science vol. 249:386–390 (1990).
Devlin et al., Random Peptide Libraries: A Source of Specific Protein Binding Molecules, Science vol. 249:404–406 (1990).
Parmley and Smith, Antibody–selectable filamentous fd phage vectors: affinity purification of target genes, Gene vol. 73:305–318 (1988).
George P. Smith, Filamentous Fusion Phage: Novel Expression Vectors That Display Cloned Antigens on the Virion Surface, Science vol. 228: 1315–1317 (1985).
Dildrop, Renate, A new classification of mouse $V_H$ sequences, Immunology Today, vol. 5:85–86 (1984).
Huse et al., Generation of a Large Comibnatorial Library of the Immunoglobuilin Repertoire in Phage Lambda, Science vol. 246:1275–1281 (1989).
Sastry et al., Cloning of the immunological repertoire in *Escherichia coli* for generation of monoclonal catalytic antibodies: Construction of a heavy chain variable region–specific cDNA library, Proc. Natl. Acad. Sci. USA vol. 86:5728–5732 (1989).
Orlandi et al., Cloning immunoglobulin variable domains for expression by the polymerase chain reaction, Proc. Natl. Acad. Sci. USA vol. 86:3833–3837 (1989).

*Primary Examiner*—Toni R. Scheiner
*Attorney, Agent, or Firm*—Campbell & Flores LLP

[57] ABSTRACT

The invention relates to methods for manipulating nucleic acids so as to optimize the binding characteristics of an encoded binding protein by providing two or more nucleic acids encoding binding proteins having at least one set of splicing sites, the set of splicing sites flanking opposite ends of one or more encoded binding domains; mixing the nucleic acids to produce a parent population of mixed nucleic acids encoding binding proteins; and randomly incorporating the binding domains between the nucleic acids through the set of splicing sites to produce a different population of nucleic acids encoding binding proteins wherein at least one binding protein is characterized by substantially different binding characteristics than a member of the parent population.

29 Claims, 1 Drawing Sheet

FIG. 1

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:1:

CGATGGCCCT CTACGAGAAC CATC                                               24

(2) INFORMATION FOR SEQ ID NO:2:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:2:

ATAATATCCC AACCTAATTT AC                                                 22

(2) INFORMATION FOR SEQ ID NO:3:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO:3:

CGACGTTGTA AAACCAGGCC AGTGGCAAGT GACG                                    34

(2) INFORMATION FOR SEQ ID NO:4:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:4:

CCACAAGAAT GGAGTTAAGC CC                                                 22

(2) INFORMATION FOR SEQ ID NO:5:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (xi) SEQUENCE DESCRIPTION: SEQ ID NO:5:

TGGTACCACC AGGTGGGACA GCCTAGGCTG TCCCACCTGG TGGTACCA                     48

(2) INFORMATION FOR SEQ ID NO:6:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:6:

ATAAACTCCA ACATCCTCAG C                                                                                                   21

OPTIMIZATION OF BINDING PROTEINS

This application is a continuation of application Ser. No. 07/631,659, filed Dec. 20, 1990, now abandoned.

BACKGROUND OF THE INVENTION

This invention relates generally to ligand-protein binding interactions and, more particularly, to methods for the optimization of antigen-antibody binding affinity.

Antibodies are heteromeric binding proteins generated by a vertebrate's immune system which bind to an antigen. The molecules are composed of two heavy and two light chains connected through disulfide bonds. Antibodies have a "Y"— shaped structure with the antigen binding portion being located at the end of both short arms of the Y. The region on the heavy and light chain polypeptides which corresponds to the antigen binding portion is known as the variable region. The binding specificity of an antibody is a composite of the antigen interactions with both heavy and light chain variable regions. The differences within this region are primarily responsible for the variation in binding specificities between antibodies.

The immune system has the capability of generating an almost infinite number of different antibodies. Such a large diversity is generated primarily through ontological recombination to form the variable regions of each chain and through differential pairing of heavy and light chains. Within the framework of the variable region of each chain are domains characterized by unusually divergent hypervariable sequences. These hypervariable region sequences are in large part responsible for antibody diversity since they constitute the antigen binding pocket within the native protein. Differences in amino acid sequences within these regions allow for the formation of different antigen-antibody binding interactions. Thus, the hypervariable variable region sequences complement the antigen functional groups and, as such, are also known as complementarity determining regions (CDRs). The ability to mimic the natural immune system by creating diverse combinations of CDR sequences would be of great value because it would allow for the rapid production of antibodies with high affinity to essentially any desired antigen. Such antibodies can be used for various diagnostic and therapeutic purposes.

Until recently, generation of antibodies against a desired molecule was accomplished only through manipulation of natural immune responses. Methods included classical immunization techniques of laboratory animals and monoclonal antibody production. Generation of monoclonal antibodies is laborious and time consuming. It involves a series of different techniques and is only performed on animal cells. Animal cells have relatively long generation times and require extra precautions to be taken to ensure viability of the cultures.

A method for the generation of a large repertoire of diverse antibody molecules in bacteria has also been described, Huse et al., Science 246:1275–1281 (1989), which is incorporated herein by reference. The method uses the bacteriophage lambda as the vector. The lambda vector is a long, linear double-stranded DNA molecule. Production of antibodies using this vector involves the cloning of heavy and light chain populations of DNA sequences into separate vectors. The vectors are subsequently combined randomly to form a single vector which directs the coexpression of heavy and light chains to form antibody fragments. A disadvantage to this method is that the antibody affinities are limited to in vivo derived affinities. This difference in affinities is due to a specific immunological affinity maturation process known as somatic mutation. Antibodies derived from recombinant libraries may not have benefited from this process. Additionally, antibody sequences may be disproportionally represented within the library due to the cloning process itself. An inherent outcome of this event can cause selection of only moderate affinity antibodies from the library if they predominate over the high affinity sequences.

There thus exists a need for a method to optimize antigen binding affinities which mimics the natural immunological processes and provides in vitro-derived antigen binding affinities different than those derived in vivo. The present invention satisfies these needs and provides related advantages as well.

SUMMARY OF THE INVENTION

The invention relates to methods for manipulating nucleic acids so as to optimize the binding characteristics of an encoded binding protein by providing two or more nucleic acids encoding binding proteins having at least one set of splicing sites, the set of splicing sites flanking opposite ends of one or more encoded binding domains; mixing the nucleic acids to produce a parent population of mixed nucleic acids encoding binding proteins; and randomly incorporating the binding domains between the nucleic acids through the set of splicing sites to produce a different population of nucleic acids encoding binding proteins wherein at least one binding protein is characterized by substantially different binding characteristics than a member of the parent population.

DETAILED DESCRIPTION OF THE INVENTION

This invention is directed to simple and efficient methods to mix binding domains between binding proteins. The method can be used to optimize binding characteristics of a desired binding protein and is advantageous in that it increases the number of possible proteins capable of binding to a particular antigen by randomly interchanging related binding domains. Interchanging domains which exhibit related functions increases the possibility of obtaining productive differences in antigen binding interactions leading to substantially different binding interactions. The binding proteins are useful in an unlimited number of diagnostic and therapeutic procedures.

In one embodiment, cloned populations of heavy and light chain antibody fragments are used to generate binding proteins toward a particular antigen having substantially different binding characteristics than the original cloned population. The antibody fragments within the original cloned population all exhibit binding specificity and affinity for the desired antigen and are thus functionally related. Novel antibodies are generated by randomly mixing different combinations of CDR sequences between the related antibodies. The CDR sequences are mixed, for example, by either single-strand nucleic acid directed mutagenesis or by introducing a set of cleavage sites, such as restriction enzyme recognition sites, at locations which flank the desired sequences to be mixed. Each cleavage site within the set should be at opposite ends of the sequences to be mixed and the termini generated after cleaving one site should not be compatible for ligation with the termini generated at the other site. Noncompatibility of the termini ensures proper orientation of the mixed sequences upon subsequent ligation. The population of encoding nucleic acids are cleaved with a cleavage reagent, such as a restriction enzyme, and then re-ligated to form random combinations of CDRs within the antibody fragment framework. In this way, individual CDRs within each heavy or light chain can be mixed or complete sets of CDRs from heavy chains can be mixed with those of light chains to produce antibodies exhibiting substantially different binding characteristics toward a particular antigen than a member within the original cloned population.

As used herein, the term "binding protein" refers to a protein which exhibits binding activity toward a particular molecule. It is understood that the term includes fragments of the polypeptide so long as binding function is retained. Such binding proteins can include single binding domain proteins as well as multi-binding domain proteins. Multi-binding domain proteins include those proteins which contain two or more discreet and noncontiguous regions along the primary structure of the polypeptide which together contribute to the overall biding activity. A specific example of multi-binding domain proteins includes heavy and light antibody chains since the binding activity of each is derived from three noncontiguous complementarity determining regions. Binding proteins can be monomeric or multimeric species. Heteromeric binding proteins are a specific example of multimeric binding proteins which are composed of at least two different subunits which together exhibit binding activity toward a particular ligand. It is understood that when referring to multimeric binding proteins that the term includes fragments of the subunits so long as assembly of the polypeptides and binding function of the assembled complex is retained. Heteromeric binding proteins include, for example, antibodies and fragments thereof such as Fab and F(ab')$_2$ portions, T cell receptors, integrins, hormone receptors and transmitter receptors.

As used herein, the term "binding domain" refers to a polypeptide or nucleic acid encoding a polypeptide whose amino acid sequence represents a specific region of a given protein and exhibits binding characteristics, by itself or in combination with other domains, similar to the binding characteristics of the native protein. The boundaries of the domains are not critical so long as binding activity is maintained. A specific example of a binding domain includes the complementarity determining region within the variable region of heavy or light chain antibody sequences.

As used herein, the term "optimization" refers to the modification of the binding characteristics of a binding protein to achieve related binding proteins having substantially different binding properties as judged by any quantifiable assay system. The term includes both increases and decreases in affinity, avidity or specificity. The optimal binding characteristics will depend on the particular application of the binding protein. For example, decreasing the affinity of a high-affinity tumor antigen binding protein can be an optimization procedure to enable penetration of the binding protein into the tumor mass. Conversely, it may be necessary to increase the affinity of binding proteins which exhibit low specificity toward a particular ligand in order to obtain optimal binding characteristics.

As used herein, the term "splicing site" refers to a predetermined region within one nucleic acid which can be used for joining to a second nucleic acid. Methods such as single strand nucleic acid directed mutagenesis, hereinafter referred to as "insertional mutagenesis," and restriction/ligation can be used for joining the two nucleic acids at the splicing site. The splicing sites are typically homologous enough to allow hybridization between complementary strands. For example, insertional mutagenesis and restriction/ligation using enzymes which produce single strand overhangs use splice sites which can hybridize between two complementary strands. Alternatively, splice sites contained within two nucleic acids can be joined without having sequence homology between complementary strands. An example of such a splice site is a restriction enzyme site which produces blunt, double-stranded ends.

As used herein, the term "set of splicing sites" refers to two or more splicing sites. In its simplest form, a set is a pair of splicing sites; however, a set can be any odd or even number of splicing sites which are used for joining nucleic acid segments. Three splicing sites is a specific example of an odd number of sites which make up a set. In this case, one of the splicing sites can be shared with each of the other two sites for independent or simultaneous use in joining nucleic acids. Replacement of adjacent CDR regions can be performed, for example, using a set of splicing sites which has two members flanking both CDR regions and a third member between the two CDR regions.

As used herein, the term "cleavage site" refers to a location within a nucleic acid in which the phosphodiester backbone is capable of being specifically broken. Cleavage sites can be, for example, restriction enzyme recognition sites such as Bst XI, Fok I and Bgl I. Also included within this definition are chemical cleavage sites.

As used herein, the term "cleaving reagent" refers to the means by which a cleavage site is cleaved. For example, if the cleavage site is a restriction enzyme recognition site then the cleaving reagent is a restriction enzyme. Cleaving reagents which leave ends which are "noncompatible for ligation" as used herein, are reagents which produce termini containing noncomplementary single strands or termini which are capable of being modified to contain noncomplementary single strands protruding from each end of a duplex nucleic acid. Any non-isoschizomeric enzyme pair can be used as well as an enzyme which recognizes the same site within the nucleic acid but cleaves the phosphodiester bonds outside of the recognition sequence or at an undefined sequence within the recognition site. Examples of such enzymes include Bst XI, Fok I and Bgl I.

The invention provides a method for the optimization of binding proteins. The method includes: (a) providing two or more nucleic acids encoding binding proteins having at least one set of splicing sites, said set of splicing sites flanking opposite ends of one or more encoded binding domains; (b) mixing said two or more nucleic acids to produce a parent population of mixed nucleic acids encoding binding proteins; and (c) randomly incorporating said binding domains between said two or more nucleic acids through said set of splicing sites to produce a different population of nucleic acids encoding binding proteins wherein at least one binding protein is characterized by substantially different binding characteristics than a member of the parent population.

The invention will be described in reference to its presently preferred embodiment: the optimization of binding affinity of antibody fragments, such as Fab and Fv, for a particular antigen. However, because the principles are the same for all binding proteins, the methods described herein can be used for the optimization of binding proteins other than antibodies without departing from the spirit of the invention. Binding proteins other than antibody fragments can include, for example, T cell receptors, integrins, hormone receptors and transmitter receptors, steroid-like hormones and DNA binding proteins.

Figure 1:
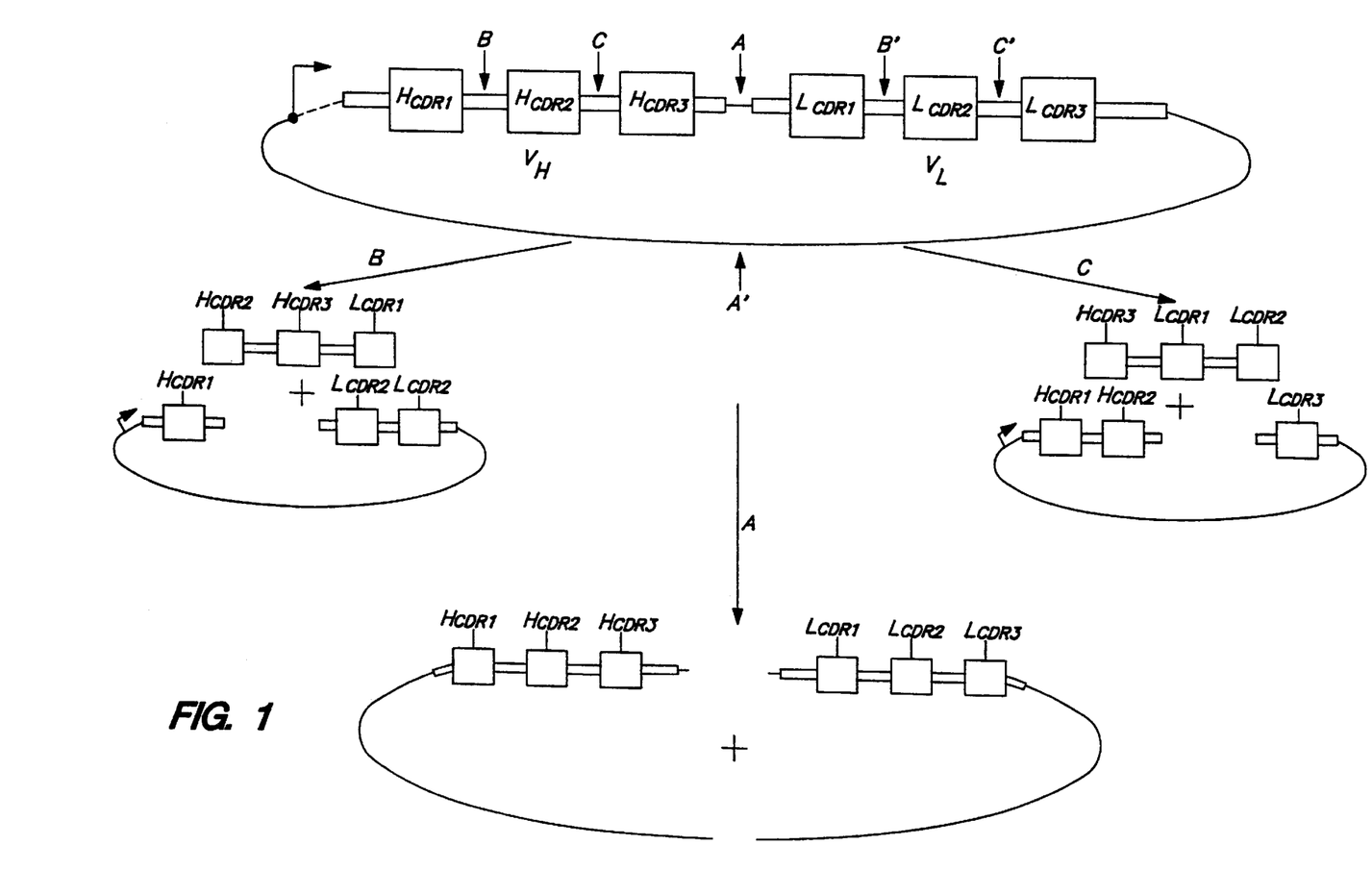
FIG. 1 diagrams the mixing of binding domains from a heteromeric binding protein. Top: A heteromeric binding protein is encoded by two polypeptides ($V_H$ and $V_L$). The binding pocket of each polypeptide consists of three distinct binding domains $H_{CDR1}$ through $H_{CDR3}$ and $L_{CDR1}$ through $L_{CDR3}$. (A) Mixing of different $V_H$ CDRs with different $V_L$ CDRs. (B) Mixing of CDRs 1 with CDRs 2 and 3 for both polypeptides. (C) Mixing of CDR 3 with CDRs 1 and 2 for both polypeptides.

The antigen binding domains within antibody molecules are known as complementarity determining regions (CDRs) and are located within the variable region of both the heavy and light chain polypeptides. There are three CDRs within each variable region (FIG. 1, top). These domains constitute the majority of the antigen binding interactions when properly folded into a native structure. CDRs are typically about 10 to 15 amino acid residues in length and are noncontiguous along the primary structure of the polypeptide backbone.

Because CDRs constitute the majority of the binding interactions between antibodies and antigens, these sequences can be mutated or interchanged with other different CDRs to generate new antibodies with substantially different binding characteristics for a particular antigen than that of the parent molecules. Optimization of binding interactions by interchanging different but related domains within an antigen binding protein is advantageous when a series of functionally related binding proteins are available to a particular antigen. Different combinations of such domains are more likely to yield productive changes in binding characteristics than random sequence changes without any restrictions on function. Therefore, binding domains which recognize the same antigen in a similar fashion as well as domains which recognize the same antigen in different ways can be randomly mixed with their cognate domains to produce novel combinations yielding substantially different binding characteristics. Mixing is the act of changing the order of binding domains by mixing together.

An example of mixing binding domains within functionally related proteins is to randomly produce all combinations of CDRs within and between heavy or light chains of related antibodies. Such random mixing can be accomplished at several levels depending on whether whole sets of CDRs, subsets or individual CDRs are used for the process. First, entire sets of CDRs (CDRs 1 through 3) within a heavy or light chain can be randomly mixed with entire sets of CDRs on the opposite chain. This mixing in effect produces new antibody fragments by pairing different heavy chains with different light chains. Second, subsets (e.g., two CDRs) or individual CDRs can be randomly mixed to produce similar antibodies with different binding characteristics due to the substitution of a fraction of the binding domains within a multi-binding domain protein. Third, antibodies selected for differential binding characteristics due to CDR mixing can be further optimized by selected mutagenesis.

The mixing of CDRs can be accomplished by a variety of means. For example, insertional mutagenesis can be used to randomly mix binding domains within a parent population of two or more nucleic acids. One or more nucleic acids within the population can be used as templates for mutagenesis. The templates can be single strand nucleic acids produced by ordinary skills using vectors such as those derived from M13. Domains to be randomly mixed with the template population can be synthesized using, for example, polymerase chain reaction (PCR) with splicing sites at each terminus which are complementary to splicing sites flanking the binding domain(s) on the template nucleic acid. The source of template material for PCR can be, for example, mRNA or cloned populations of cDNAs. Splicing sites complementary to flanking sequences insures proper orientation of the inserted sequences. Alternatively, chemical synthesis methods can be employed to generate the binding domains to be mixed and their corresponding splicing sites.

Synthesized binding domains are denatured, for example, with heat or alkali to produce single strands if they are in double strand form and annealed with templates. Hybridization through complementary sequences is very specific and therefore advantageous for joining two nucleic acids together at predetermined sites. The criteria for determining where splicing sites should be located is described below with reference to splicing sites which are cleavage sites. The annealed splicing sites can be used as substrates for primer extension to produce double-stranded nucleic acids. If the annealed splicing sites are relatively large and able to maintain a stable duplex, the annealed population of nucleic acids can be directly introduced into a host organism. Biosynthetic machinery within the organism is capable of producing double-stranded nucleic acids. Populations of nucleic acids encoding binding proteins produced in such a way will have their binding domains randomly incorporated within the parent population of binding proteins to produce a different population of nucleic acids where at least one encoded binding protein is characterized by substantially different binding characteristics than a member of the parent population.

Mixing of CDRs can also be accomplished by introducing sets of splicing sites, such as cleavage sites, at predetermined locations within the nucleic acids encoding the binding proteins. This is shown schematically in FIG. 1 where the sets of cleavage sites are represented as A and A', B and B' or C and C'. The cleavage sites can be, for example, restriction enzyme recognition sequences. Such recognition sequences can be introduced into the nucleic acids by methods well known in the art. Site-directed mutagenesis as described by Kunkle et al., Proc. Natl. Acad. Sci. U.S.A., 82:488–492 (1985), which is incorporated herein by reference, is one such method. The cleavage sites should be selected so that the termini produced at the two ends after cleaving are not compatible for subsequent ligation. Non-compatible termini ensures that the fragments will come together in the proper orientation after mixing of CDR sequences. For example, if a vector encoding heavy ($V_H$) and light ($V_L$) chain fragments (FIG. 1, top) is cleaved with cleaving reagent A, the termini produced will be A and A'. A termini are compatible with other A termini but not with A' termini. Upon subsequent ligation, only As will be joined with other As and similarly, A's with other A's, thus reconstructing the original orientation of the $V_H$ and $V_L$ fragments. Sets of cleavage sites should also be selected so that they are uniquely found at their preselected location. Redundant cleavage sites encoded at other locations within the vector or coding region of the binding proteins will also be cleaved during mixing. Cleavage at these undesirable redundant sites will generate extra fragments which will essentially be eliminated during the mixing process.

Splicing sites selected from restriction enzyme recognition cleavage sites and sequences having complementary homology are advantageous to use for the optimization of binding affinities, however, alternative sites can also be used. For example, chemical cleavage methods known to one skilled in the art can be used which specifically cleave at predetermined locations. Restriction enzyme recognition sites, however, are well characterized and their cleaving reagents, restriction enzymes, are commercially available at inexpensive prices. Several restriction enzymes exist which recognize a specific sequence but cleave the nucleic acid outside of the recognition sequence or at an undefined sequence within the recognition site. This mechanism offers an additional advantage in that the same enzyme can be used to produce different termini at two different cleavage sites. For example, Fok I is a restriction enzyme which recognizes the sequence 5'-GGATG-3' but cleaves the phosphodiester backbone of double-stranded DNA nine and thirteen bases downstream for the top and bottom strands, respectively. Therefore, the sequences at the distal cleavage sites will determine ligation compatibility and not the invariant recognition sequence.

The cleavage sites introduced into nucleic acids encoding the binding proteins should be positioned such that they flank opposite ends of the binding domains to be mixed. The sites should also be positioned at locations which are nonessential for function of either the binding protein, expression sequences or vector sequences. If a cleavage site is to be placed within an essential coding region, then the site should be chosen so as to allow only conservative substitutions of amino acid residues. Splicing sites using complementary homology should be chosen such that the sequence is sufficiently homologous within all members of the population to allow hybridization. For the mixing of entire sets of $V_H$ CDRs with sets of $V_L$ CDRs, the cleavage sites should be located outside of all three CDRs for each chain. In FIG. 1, top, the pair of cleavage sites A and A' depicts this arrangement for adjacent $V_H$ and $V_L$ sequences. The A cleavage site is located between the $V_H$ CDR3 ($H_{CDR3}$) and the $V_L$ CDR1 ($L_{CDR1}$). The A' cleavage site is located on the other side of the vector between $H_{CDR1}$ and $L_{CDR3}$. The exact positioning of cleavage site sets can vary depending on the organization of the domains to be mixed. One skilled in the art will know where to introduce the sets of cleavage sites or determine the appropriate complementary sequence so as to flank the binding domains and allow mixing.

Two or more nucleic acids encoding $V_H$ and $V_L$ antibody chains can be mixed to produce a random population encoding all the domains to be mixed. Mixing of $V_H$ CDRs with $V_L$ CDRs using cleavage sites as splicing sites is performed by cleaving the mixed population of nucleic acids with cleaving reagent A (FIG. 1A) and then ligating the mixture to reform random combinations of $V_H$ CDRs with $V_L$ CDRs. Antibodies which exhibit differential binding affinities compared to the parent molecules can be selected by expressing the new population of encoding nucleic acids in a procaryotic or eucaryotic expression system using methods well known in the art.

Nucleic acids encoding the binding proteins can be cloned into any of a variety of vectors well known in the art. Alternatively, the nucleic acids can be initially cloned into a vector which enables both the optimization procedures described herein and the expression of polypeptides which constitutes the binding protein (FIG. 1, top). For heteromeric binding proteins, coexpression of two or more nucleic acid sequences is generally performed to produce separate polypeptides. The separate polypeptides self-assemble post- or co-translationally to form the functional molecule. Coexpression can also be accomplished, for example, by expressing the subunit polypeptides as a single chain which are linked together and are still capable of assembling into an heteromeric binding protein. A specific example of the coexpression of linked polypeptides is the expression of heavy and light chain antibody fragment polypeptides with a flexible peptide or polypeptide linker joining the two subunits into a single chain. The linker is flexible enough to allow association of heavy and light chain portions into a functional Fab fragment, U.S. Pat. No. 4,946,778, which is incorporated herein by reference.

Vectors which can be used for coexpression are known or can be constructed by those skilled in the art. Likewise, vectors which can be used for the expression of monomeric binding proteins are known or can be constructed by those skilled in the art. Such vectors should contain all expression elements necessary for the transcription, translation, regulation and sorting of the polypeptides which make up the binding proteins. Such vectors may also include mechanisms for recovery in a different form. Phagemids are a specific example of this because they can be used either as plasmids or as phage vectors. The vectors can be for use either in procaryotic or eucaryotic host systems so long as the expression elements are of a compatible origin. One of ordinary skill in the art will know which host systems are compatible with a particular vector. Thus, the invention provides vectors, host cells transformed with the vectors and binding proteins produced from the host cells which contain nucleic acids encoding a binding protein produced by the above method for the optimization.

For the mixing of individual CDRs or subsets of CDRs, a strategy identical to that described above for mixing whole sets of CDRs can be employed. For example, CDR 1 can be randomly mixed with CDRs 2 and 3 in both $V_H$ and $V_L$ encoding portions by using splicing sites between CDRs 1 and 2 of both $V_H$ and $V_L$. The two splicing sites introduced constitute the set of sites which can be used for the mixing process and are depicted in FIG. 1B as sites B and B'. The set of splicing sites therefore flanks $H_{CDR1}$ and $L_{CDR2}$ since the binding domains in between are those which are to be mixed. Nucleic acids having splicing sites between CDRs 1 and 2, for example, can be mixed to produce a random population. Sequences between the splicing sites are randomly incorporated among the population by, for example, insertional mutagenesis or restriction/ligation. For insertional mutagenesis, the population of nucleic acids should first be annealed with chosen template molecules. For restriction/ligation, cleaving the nucleic acids first at position B and B' will release the binding domains to be mixed ($H_{CDR1}$, $H_{CDR2}$, $L_{CDR1}$; FIG. 1B). Subsequent ligation of the mixed and cleaved population brings together random combinations of CDR1 with CDRs 2 and 3 for both the $V_H$ and $V_L$ chains. The novel combinations of binding domains can be screened by expression for productive changes in binding affinity as described above. Such methods of screening include, for example, ELISA, immunoblots, panning, plaque lifts, equilibrium dialysis and competition assays. These methods are well known to one skilled in the art and are described, for example, in Harlow et al., Antibodies: A Laboratory Manual, Cold Spring Harbor Laboratory, Cold Spring Harbor (1988), which is incorporated herein by reference.

Binding domains other than CDR1 can also be mixed. For example, CDR3 can be mixed with CDRs 1 and 2 using the methods described herein. By using splicing sites between CDRs 2 and 3 in both the $V_H$ and $V_L$ sequences, the binding domains internal to these sites can be mixed (FIG. 1C). Populations of nucleic acids encoding binding proteins with related functions can be mixed, treated with cleaving reagent C and subsequently re-ligated to produce random combinations of binding domains. Alternatively, templates and synthesized binding domains having splicing sites located at C can be mixed with random incorporation of the binding domains by insertional mutagenesis. Similarly, CDR2 can be randomly mixed with CDRs 1 and 3. For example, a set of splicing sites containing three members can be used and is advantageously performed by insertional mutagenesis. Two of the splicing sites can be located external to CDR2 on both the heavy and light chain sequences. The third splicing site can be located between the CDRs, for example, within the sequences spanning $H_{CDR3}$ and $L_{CDR1}$. Likewise, adjacent CDRs can be mixed by having splicing sites located externally and a common site located between them. Annealing of nucleic acids having splicing sites with the above described organization will result in the random incorporation of, for example, $H_{CDR2}$ and $L_{CDR2}$ within the population. Additionally, there are some bacterial strains which exist, such as DH10B (Life Technologies, Bethesda, Md.) which demonstrate the occurrence of DNA repair functions before DNA replication. In these strains, approximately equal frequencies of sequences corresponding to the synthesized nucleic acids and template nucleic acids will be obtained. Thus numerous different templates can be used with numerous different synthesized nucleic acids to obtain all possible permutations independently of each other.

The binding proteins selected which exhibit optimized binding characteristics compared to the unmixed, parent molecules can be further optimized by selected mutagenesis. Although the combinations obtained after mixing of related binding domains can provide binding proteins having beneficial characteristics due to differential antigen binding characteristics, those molecules selected may not necessarily encode the best sequences required for optimal antigen binding properties. The selected sequences are simply the optimal sequences which can be obtained from the starting parent molecules. Selected mutagenesis incorporating random amino acid changes, or a desired bias of amino acid changes based on the known sequence, can further provide productive changes which yield more beneficial binding characteristics.

Mutagenesis can be performed by standard methods in the art using oligonucleotides designed to incorporate specific changes at predetermined positions within the encoding nucleic acids. Alternatively, the oligonucleotides used for mutagenesis can be synthesized by a method which produces diverse amino acid codons but is biased toward a predetermined sequence; the predetermined sequence being one or all of the binding domains within an optimized binding protein. This method of synthesis is advantageous to use for creating mutant oligonucleotides when a significant number of amino acid codon positions are to be of a specified sequence. The method is disclosed in detail in U.S. patent application Ser. No. 07/573,648 which is explicitly incorporated herein by reference. Briefly, the method entails oligonucleotide synthesis using two reaction columns. In the first column, the nucleotide sequence of the specified codon is sequentially synthesized. In the second column, a degenerate codon is synthesized by coupling a mixture of all four nucleotides at the first and second monomer positions of the codon. The codon is completed by coupling a mixture of either guanine and thymine or cytosine and adenine nucleotides at the third monomer position. Mixing the reaction products of the two columns yields a population of oligonucleotides containing both the predetermined sequence and the random sequence at the desired position. Synthesis can proceed by using this mixture for coupling additional predetermined sequences, or, by further dividing into two reaction columns for synthesis of additional random sequences. By using such mutant oligonucleotides, changes can be made in the binding domains and the resultant binding proteins can be selected for optimized binding characteristics using standard recombinant expression methods as described above.

The following examples are intended to illustrate but not limit the invention.

EXAMPLE I

Systematic Mixing of CDRs for the Optimization of Antigen Binding

This example shows the optimization of Fab binding affinities through successive rounds of mixing $V_H$ and $V_L$ CDRs and selection of molecules demonstrating higher affinities for human β-endorphin than those Fab fragments obtained in previous rounds.

Incorporation of Restriction Sites for CDR Mixing

Fab fragments selected from recombinant cell surface expression libraries and having affinity for the human β-endorphin peptide were used for optimization protocols. In this system, which is described in detail in U.S. patent application Ser. No. 07/590,219 and incorporated herein by reference, heavy and light chain sequences are coexpressed on the surface of filamentous bacteriophage M13 from a dicistronic operon under the transcriptional control of the Lac promoter/operator. Unless otherwise stated, all recombinant methods performed for routine manipulations, such as phage culturing, vector isolation, DNA restriction, ligation and transformation and the like, were standard methods known to one skilled in the art. Such methods can be found in SanBrook et al., Molecular Cloning: A Laboratory Manual, Cold Spring Harbor Laboratory, Cold Spring Harbor, 1989, and in Ausubel et al., Current Protocols in Molecular Biology, John Wiley and Sons, New York, 1989, both of which are incorporated herein by reference.

To obtain the restriction sites used for mixing CDRs, mutagenesis was performed where necessary to give the restriction patterns diagrammed in FIG. 1. "A" and "A'" restriction sites correspond to Bst XI, "B" and "B'" correspond to Dra III and "C" and "C'" correspond to Fok I. Only three sites, corresponding to A, A' and B' in FIG. 1, were necessary to incorporate by mutagenesis since the remaining sites are found naturally in most heavy and light chain sequences. However, Dra III and a Fok I sites were removed from the vector using the mutant oligonucleotides 5'-CGATGGCCCTCTACGAGAACCATC-3' (SEQ ID NO: 1) AND 5'-ATAATATCCCAACCTAATTTAC-3' (SEQ ID NO: 2). Mutagenesis is performed using the method of Kunkel et al., Meth. Enzymol. 154:367–382 (1987), which is incorporated herein by reference. The reagents strains and protocols were obtained from a Bio Rad Mutagenesis Kit (Bio Rad, Richmond, Calif.) and mutagenesis is performed as recommended by the manufacturer. Briefly, an overnight culture of CJ236 is inoculated (1 ml) into 50 μls of SOB-CAP and grown to $OD_{600}$=0.3. Phage containing the template to be mutagenized are diluted 1:100 and 10 μl is added to the culture. Incubation is continued at 37° C. for an additional 4 hours. Cultures are centrifuged twice at 12,000 rpm for 15 minutes at 4° C. and the supernatant is transferred to a new tube. RNase A is added (15 μl of 10 mg/ml) followed by 7.5 mls of 20% PEG 8000 in 3.5 M $NH_4OAc$. The suspension is incubated on ice for 30 minutes and centrifuged once as described above. The pellet is resuspended in 200 μl high salt buffer (300 mM NaCl, 100 mM Tris, pH 8.0, 1 mM EDTA) and filtered on both XL1-Blue™ (Stratagene, La Jolla, Calif.) and on CJ236. CJ236 phage stocks are extracted with an equal volume of phenol/chloroform/isoamyl alcohol (1:1:1/48) followed by back extraction with $dH_2O$. These uracil-containing nucleic acids are ethanol precipitated, washed, resuspended in 20 μl dH$_2$O and quantitated. The uracil-containing template (233 μg) is mixed with 20 ng (in 1 μl) of phosphorylated mutant oligonucleotide and 1 μl of 10× annealing buffer (200 mM Tris, pH 7.4, 20 mM MgCl$_2$, 500 mM NaCl) in 10 μl final volume, heated to 70° C. and slow cooled to room temperature. The reactions are placed on ice and 1 μl of 10× synthesis buffer (4 mM each dNTP, 7.5 mM ATP, 175 mM Tris, pH 7.4, 37.5 mM MgCl$_2$, 215 mM DTT), 1 μl T4 DNA ligase (3–5 units) and 1 μl T4 Dna polymerase is added. The reactions are incubated for 5 minutes on ice followed by 90 minutes at 37° C. Reactions are stopped by addition of 90 μl of stop buffer (10 mM Tris, pH 8.0, 10 mM EDTA) and transformed into XL1-Blue™ cells.

The sequences of the mutant oligonucleotides are given in Table I where the underlined portion indicates the incorporated restriction enzyme site. The oligonucleotides correspond to the non-coding strand of the $V_h$, $V_l$ or vector sequence. All mutations are confirmed by restriction enzyme digestion and sequence analysis. Sequencing is performed by the method of Sanger et al., Proc. Natl. Acad. Sci. U.S.A. 74:5463–5467 (1977), using Sequenase$^R$ version 2.0 DNA sequencing kit as recommended by the manufacturer.

TABLE I

Oligonucleotide Sequences used for Mutagenesis

| Oligonucleotide | Incorporated Restriction Site | Sequence (5' to 3') |
| --- | --- | --- |
| A | Bst XI | 5'-CGACGTTGTAAAACC AGGCCAGTGGCAAGTGA CG-3' (SEQ ID NO:3) |
| A' | Bst XI | 5'-CCACAAGAATGGAG TTAAGCCC-3' (SEQ ID NO:4) |
| B' | Dra III | 5'-TGGTACCACCAGG TGGGACAGCCTAGGCTG TCCCACCTGGTGGTAC CA-3' (SEQ ID NO:5) |
| C' | Fok I | 5'-ATAAACTCCAACAT CCTCAGC-3' (SEQ ID NO:6) |

Optimization of Binding Affinity by CDR Mixing

For optimization of Fab binding affinities, three successive rounds of CDR mixing is performed. Each round of mixing expands the number of combinations which can be tested by using the newly generated antibodies in different CDR combinations with themselves and with the original set of selected Fab fragments.

For the first set of combinations, heavy chain CDRs are mixed with different light chain CDRs between antibodies exhibiting antigen binding affinity for human β-endorphin. This mixing efficiently allows testing of different heavy chain antigen binding sequences with different complementary light chain antigen binding sequences.

For the mixing of heavy and light chain CDRs, the mutagenized vectors described above encoding the antibody sequences were digested with Bst XI. Equal amounts of each vector is combined to yield a final amount between 5 and 10 μg of total DNA. The digestions are checked for completion by aganose gel electrophoresis. Reactions are stopped by extracting once with an equal volume of phenol/chloroform, once with chloroform, followed by ethanol precipitation. The pellets are washed with 70% ethanol, dried under vacuum and resuspended in 8.5 μl distilled or deionized water (dH$_2$O). One μl of 10× ligase buffer (50 mM Tris-HCl, pH 7.8, 10 mM MgCl$_2$, 20 mM DTT, 1 mM ATP, 50 μg/ml BSA) is added, followed by 0.5 μl of T4 DNA ligase (2 U/μl; Bethesda Research Laboratories, Gaithersburg, Md.). The ligations are incubated at 16° C. overnight or for 2 hours at room temperature prior to electroporation into a compatible host strain.

E. coli MK30-3 is electroporated as described by Smith et al., Focus 12:38–40 (1990) which is incorporated herein by reference. The cells are prepared by inoculating a fresh colony of MK30-3 into 5 mls of SOB without magnesium (20 g bacto-tryptone, 5 g bacto-yeast extract, 0.584 g NaCl, 0.186 g KCl, dH$_2$O to 1,000 mls) and grown with vigorous aeration overnight at 37° C. SOB without magnesium (500 ml) is inoculated at 1:1000 with the overnight culture and grown with vigorous aeration at 37° C. until the OD$_{550}$ is 0.8 (about 2 to 3 h). The cells are harvested by centrifugation at 5,000 rpm (2,600 ×g) in a GS3 rotor (Sorvall, Newtown, Conn.) at 4° C. for 10 minutes, resuspended in 500 ml of ice-cold 10% (v/v) sterile glycerol, centrifuged and resuspended a second time in the same manner. After a third centrifugation, the cells are resuspended in 10% sterile glycerol at a final volume of about 2 ml, such that the OD$_{550}$ of the suspension was 200 to 300. Usually, resuspension is achieved in the 10% glycerol that remained in the bottle after pouring off the supernate. Cells are frozen in 40 μl aliquots in microcentrifuge tubes using a dry ice-ethanol bath and stored frozen at −70° C.

Frozen cells are electroporated by thawing slowly on ice before use and mixing with about 10 pg to 500 ng of vector per 40 μl of cell suspension. A 40 μl aliquot is placed in an 0.1 cm electroporation chamber (Bio-Rad, Richmond, Calif.) and pulsed once at 0° C. using 4 kω parallel resistor 25 μF, 1.88 KV, which gives a pulse length (τ) of ~4 ms. A 10 μl aliquot of the pulsed cells are diluted into 1 ml SOC (98 mls SOB plus 1 ml of 2 M MgCl$_2$ and 1 ml of 2 M glucose) in a 12-×75-mm culture tube, and the culture is shaken at 37° C. for 1 hour prior to culturing in selective media. Briefly, the above 1 ml library cultures are grown up by diluting 50-fold into 2XYT media (16 g tryptone, 10 g yeast extract, 5 g NaCl) and culturing at 37° C. for 5–8 hours. The bacteria are pelleted by centrifugation at 10,000 ×g. The supernatant containing phage is transferred to a sterile tube and stored at 4° C.

Purified phage expressing on their surface coat the newly created Fab fragments are prepared from 50 ml liquid cultures of XL1 Blue™ cells (Stratagene, La Jolla, Calif.) which had been infected at a m.o.i. of 10 from the phage stocks stored at 4° C. The cultures are induced with 2 mM IPTG. Supernatants are cleared by two centrifugations, and the phage are precipitated by adding 1/7.5 volumes of PEG solution (25% PEG-8000, 2.5 M NaCl), followed by incubation at 4° C. overnight. The precipitate is recovered by centrifugation for 90 minutes at 10,000 ×g. Phage pellets are resuspended in 25 ml of 0.01 M Tris-HCl, pH 7.6, 1.0 mM EDTA, and 0.1% Sarkosyl and then shaken slowly at room temperature for 30 minutes. The solutions are adjusted to 0.5 M NaCl and to a final concentration of 5% polyethylene glycol. After 2 hours at 4° C., the precipitates containing the phage are recovered by centrifugation for 1 hour at 15,000 ×g. The precipitates are resuspended in 10 ml of NET buffer (0.1 M NaCl, 1.0 mM EDTA, and 0.01 M Tris-HCl, pH 7.6), mixed well, and the phage repelleted by centrifugation at 170,000 ×g for 3 hours. The phage pellets are resuspended overnight in 2 ml of NET buffer and subjected to cesium chloride centrifugation for 18 hours at 110,000 ×g (3.86 g of cesium chloride in 10 ml of buffer). Phage bands are collected, diluted 7-hold with NET buffer, recentrifuged at 170,000 ×g for 3 hours, resuspended, and stored at 4° C. in 0.3 ml of NET buffer containing 0.1 mM sodium azide.

Binding affinity is assessed by panning surface expression phage on dishes coated with human β-endorphin. β-endorphin is attached to streptavidin coated dishes following biotinylation and absorption against phage grown in the presence of uracil in a Sup E ung dut strain such as RZ1032. Phage grown in this way insures that any phage remaining after blocking will not survive under normal growth conditions and therefore will not interfere with panning. Alternatively, standard reverse immunoscreening methods using labeled antigen can also be used. The biotinylating reagents are dissolved in dimethylformamide at a ratio of 2.4 mg solid NHS-SS-Biotin (sulfosuccinimidyl 2-(biotinamido)ethyl-1,3'-dithiopropionate; Pierce, Rockford, Ill.) to 1 ml solvent and used as recommended by the manufacturer. Small-scale reactions are accomplished by mixing 1 µl dissolved reagent with 43 µl of 1 mg/ml β-endorphin diluted in sterile bicarbonate buffer (0.1 M NaHCO$_3$, pH 8.6). After 2 hours at 25° C., residual biotinylating reagent is reacted with 500 µl 1 M ethanolamine (pH adjusted to 9 with HCl) for an additional 2 hours. The entire sample is diluted with 1 ml TBS containing 1 mg/ml BSA, concentrated to about 50 µl on a Centricon 30 ultrafilter (Amicon), and washed on the same filter three times with 2 ml TBS and once with 1 ml TBS containing 0.02% NaN$_3$ and 7×10$^{12}$ UV-inactivated blocking phage (see below); the final retentate (60–80 µl) is stored at 4° C. β-endorphin biotinylated with the NHS-SS-Biotin reagent is linked to biotin via a disulfide-containing chain.

For panning, polystyrene petri plates (60×15 mm) are incubated with 1 ml of 1 mg/ml of streptavidin (BRL) in 0.1 M NaHCO$_3$ pH 8.6–0.02% NaN$_3$ in a small, air-tight plastic box overnight in a cold room. The next day streptavidin is removed and replaced with at least 10 ml blocking solution (29 mg/ml of BSA; 3 µg/ml of streptavidin; 0.1 M NaHCO$_3$ pH 8.6–0.02% NaN$_3$) and incubated at least 1 hour at room temperature. The blocking solution is removed and plates are washed rapidly three times with Tris buffered saline containing 0.5% Tween 20 (TBS-0.5% Tween 20).

Selection of phage expressing antibody fragments which bind β-endorphin is performed with 5 µl (2.7 µg β-endorphin) of blocked biotinylated β-endorphin reacted with a 50 µl portion of the library. Each mixture is incubated overnight at 4° C., diluted with 1 ml TBS-0.5% Tween 20, and transferred to a streptavidin-coated petri plate prepared as described above. After rocking 10 minutes at room temperature, unbound phage are removed and plates washed ten times with TBS-0.5% Tween 20 over a period of 30–90 minutes. Bound phage are eluted from plates with 800 µl sterile elution buffer (1 mg/ml BSA, 0.1 M Hl, pH adjusted to 2.2 with glycerol) for 15 minutes and eluates neutralized with 48 µl 2 M Tris (pH unadjusted). A 20 µl portion of each eluate is titered on MK30-3 concentrated cells with dilutions of input phage.

A second round of panning is performed by treating 750 µl of first eluate from the library with 5 mM DTT for 10 minutes to break disulfide bonds linking biotin groups to residual biotinylated binding proteins. The treated eluate is concentrated on a Centricon 30 ultrafilter (Amicon), washed three times with TBS-0.5% Tween 20, and concentrated to a final volume of about 50 µl. Final retentate is transferred to a tube containing 5.0 µl (2.7 µg β-endorphin) blocked biotinylated β-endorphin and incubated overnight. The solution is diluted with 1 ml TBS-0.5% Tween 20, panned, and eluted as described above on fresh streptavidin-coated petri plates. The entire second eluate (800 µl) is neutralized with 48 µl 2 M Tris, and 20 µl is titered simultaneously with the first eluate and dilutions of the input phage. If necessary, further rounds of panning can be performed to obtain homogeneous populations of phage. Additionally, phage can be plaque purified if reagents are available for detection.

The phage selected by panning are characterized by DNA sequencing of the Fab encoding sequences. Templates are prepared for sequencing by inoculating a 1 ml culture of 2XYT containing a 1:100 dilution of an overnight culture of XL1 with an individual plaque from the purified population. The plaques are picked using a sterile toothpick. The culture is incubated at 37° C. for 5–6 hours with shaking and then transferred to a 1.5 ml microfuge tube. 200 µl of PEG solution is added, followed by vortexing and placed on ice for 10 minutes. The phage precipitate is recovered by centrifugation in a microfuge at 12,000 ×g for 5 minutes. The supernatant is discarded and the pellet is resuspended in 230 µl of TE (10 mM Tris-HCl, pH 7.5, 1 mM EDTA) by gently pipeting with a yellow pipet tip. Phenol (200 µl) is added, followed by a brief vortex and microfuged to separate the phases. The aqueous phase is transferred to a separate tube and extracted with 200 µl of phenol/chloroform (1:1) as described above for the phenol extraction. A 0.1 volume of 3 M NaOAc is added, followed by addition of 2.5 volumes of ethanol and precipated at −20° C. for 20 minutes. The precipated templates are recovered by centrifugation in a microfuge at 12,000 ×g for 8 minutes. The pellet is washed in 70% ethanol, dried and resuspended in 25 µl TE. Sequencing was performed using a Sequenase™ sequencing kit following the protocol supplied by the manufacturer (U.S. Biochemical, Cleveland, Ohio).

The second round of CDR mixing entails randomly combining different CDR combinations within heavy and light chain populations of the selected antigen binding fragments. CDR 2 and 3 sequence were mixed within heavy and light chain populations with different CDR 1 sequences. The antibodies obtained from both the heavy and light chain combinations and from the initially selected antibodies were used for these optimization procedures.

Although an initial round of optimization has already been performed, the vectors containing selected Fab sequences still encode the restriction enzyme sites incorporated by mutagenesis. Therefore, equal amounts of each vector are combined (5–10 µg total) and digested to completion with Fok I. The subsequent steps of ligation, electroporation and screening are performed as described above.

The third round of CDR mixing entails randomly combining CDRs 1 and 2 within heavy and light chain populations with different CDR 3 sequences. All previously obtained antibodies selected for binding affinity to human β-endorphin were mixed at equal amounts and digested with Bgl I as described previously. Similarly, the ligations and screening were also performed as described above. Quantitation of the binding affinities is performed by equilibrium dialysis against labeled β-endorphin and Schatand plot analysis.

Although the invention has been described with reference to the presently-preferred embodiment, it should be understood that various modifications can be made by those skilled in the art without departing from the invention. Accordingly, the invention is limited only by the following claims.

I claim:

1. A method for manipulating nucleic acids so as to increase the binding of an encoded antibody to a particular ligand, said method comprising the steps of:
   (a) providing two or more nucleic acids encoding different antibodies all having selective binding for said particular ligand, said nucleic acids having at least one set of splicing sites, said set of splicing sites flanking opposite ends of one or more encoded CDRs, wherein the binding activity of at least one encoded antibody is known;
   (b) mixing said two or more nucleic acids to produce a parent population of mixed nucleic acids encoding said antibodies;
   (c) randomly incorporating said one or more encoded CDRs between said two or more nucleic acids through said set of splicing sites to produce a different population of nucleic acids than said parent population, wherein at least one antibody encoded by said different population is characterized by having increased binding to the particular ligand as compared to the antibody having the known binding activity; and (d) identifying at least one of the antibodies having increased binding to the particular ligand as compared to the antibody having the known binding activity.

2. The method of claim 1, wherein step (a) further comprises synthesis of at least one nucleic acid by enzymatic polymerization.

3. The method of claim 2, wherein said enzymatic polymerization is a polymerase chain reaction.

4. The method of claim 1, wherein step (a) further comprises chemical synthesis of at least one nucleic acid.

5. The method of claim 1, wherein step (c) further comprises:

(c1) introducing at least one set of cleavage sites within said parent population of mixed nucleic acids at said splicing sites;

(c2) cleaving said cleavage sites with a cleaving reagent to produce termini at each splicing site which are non-compatible for ligation and releasing said one or more encoded CDRs from said nucleic acids encoding said antibodies; and (c3) ligating said released one or more encoded CDRs to said nucleic acids encoding antibodies.

6. The method of claim 2, wherein step (c) further comprises annealing single strand regions of said splicing sites between said two or more nucleic acids, said splicing sites having sufficient nucleotide sequence identity between complementary strands to allow specific hybridization.

7. The method of claim 6, wherein said two or more nucleic acids are single-stranded.

8. The method of claim 4, wherein step (c) further comprises annealing single-stranded regions of said splicing sites between said two or more nucleic acids, said splicing sites having sufficient nucleotide sequence identity between complementary strands to allow specific hybridization.

9. The method of claim 8, wherein said two or more nucleic acids are single-stranded.

10. The method of claim 5, wherein said set of cleavage sites are restriction enzyme recognition sites.

11. The method of claim 10, wherein said restriction enzyme recognition sites are selected from the group consisting of Bst XI, Fok I and Dra III.

12. The method of claim 5, wherein said cleaving reagent is a restriction enzyme.

13. A population of nucleic acids encoding antibodies, said population of nucleic acids produced by a process, comprising the steps of:

(a) providing two or more nucleic acids encoding different antibodies all having selective binding for said particular ligand, said nucleic acids having at least one set of splicing sites, said set of splicing sites flanking opposite ends of one or more encoded CDRs, wherein the binding activity of at least one encoded antibody is known;

(b) mixing said two or more nucleic acids to produce a parent population of mixed nucleic acids encoding said antibodies; and (c) randomly incorporating said one or more encoded CDRs between said two or more nucleic acids through said set of splicing sites to produce a different population of nucleic acids than said parent population, wherein at least one antibody is characterized by different binding characteristics than the antibody having the known binding activity.

14. A population of vectors containing nucleic acids encoding antibodies, said population of vectors produced by a process, comprising the steps of:

(a) providing two or more nucleic acids encoding different antibodies all having selective binding for said particular ligand, said nucleic acids having at least one set of splicing sites, said set of splicing sites flanking opposite ends of one or more encoded CDRs, wherein the binding activity of at least one encoded antibody is known;

(b) mixing said two or more nucleic acids to produce a parent population of mixed nucleic acids encoding said antibodies;

(c) randomly incorporating said one or more encoded CDRs between said two or more nucleic acids through said set of splicing sites to produce a different population of nucleic acids than said parent population, wherein at least one antibody is characterized by different binding characteristics than the antibody having the known binding activity; and (d) inserting said different population of nucleic acids encoding said antibodies into vectors.

15. A population of host cells transformed with the population of vectors of claim 14.

16. A method for manipulating nucleic acids so as to decrease the binding of an encoded antibody to a particular ligand, said method comprising the steps of:

(a) providing two or more nucleic acids encoding different antibodies all having selective binding for said particular ligand, said nucleic acids having at least one set of splicing sites, said set of splicing sites flanking opposite ends of one or more encoded CDRs, wherein the binding activity of at least one encoded antibody is known;

(b) mixing said two or more nucleic acids to produce a parent population of mixed nucleic acids encoding said antibodies;

(c) randomly incorporating said one or more encoded CDRs between said two or more nucleic acids through said set of splicing sites to produce a different population of nucleic acids than said parent population, wherein at least one antibody encoded by said different population is characterized by having decreased binding to the particular ligand as compared to the antibody having the known binding activity; and (d) identifying at least one of the antibodies having decreased binding to the particular ligand as compared to the antibody having the known binding activity.

17. The method of claim 16, wherein step (a) further comprises synthesis of at least one nucleic acid by enzymatic polymerization.

18. The method of claim 17, wherein said enzymatic polymerization is a polymerase chain reaction.

19. The method of claim 16, wherein step (a) further comprises chemical synthesis of at least one nucleic acid.

20. The method of claim 16, wherein step (c) further comprises:

(c1) introducing at least one set of cleavage sites within said parent population of mixed nucleic acids at said splicing sites;

(c2) cleaving said cleavage sites with a cleaving reagent to produce termini at each splicing site which are non-compatible for ligation and releasing said one or more encoded CDRs from said nucleic acids encoding said antibodies; and (c3) ligating said released one or more encoded CDRs to said nucleic acids encoding antibodies.

21. The method of claim 17, wherein step (c) further comprises annealing single strand regions of said splicing sites between said two or more nucleic acids, said splicing sites having sufficient nucleotide sequence identity between complementary strands to allow specific hybridization.

22. The method of claim 21, wherein said two or more nucleic acids are single-stranded.

23. The method of claim 19, wherein step (c) further comprises annealing single-stranded regions of said splicing sites between said two or more nucleic acids, said splicing sites having sufficient nucleotide sequence identity between complementary strands to allow specific hybridization.

24. The method of claim 23, wherein said two or more nucleic acids are single-stranded.

25. The method of claim 20, wherein said set of cleavage sites are restriction enzyme recognition sites.

26. The method of claim 25, wherein said restriction enzyme recognition sites are selected from the group consisting of Bst XI, Fok I and Dra III.

27. The method of claim 20, wherein said cleaving reagent is a restriction enzyme.

28. The method of claim 1, wherein steps (a) through (d) are repeated one or more times to further increase the binding of said antibody to said particular ligand.

29. The method of claim 16, wherein the steps (a) through (d) are repeated one or more times to further decrease the binding of said antibody to said particular ligand.

* * * * *

UNITED STATES PATENT AND TRADEMARK OFFICE
CERTIFICATE OF CORRECTION

PATENT NO.  : 5,955,358
DATED       : September 21, 1999
INVENTOR(S) : William D. Huse It is certified that error appears in the above-identified patent and that said Letters Patent is hereby corrected as shown below:

Column 6,
Line 46, please delete "only As" and replace with -- only A's --.
Line 47, please delete "only As" and replace with -- only A's --.

Column 10,
Line 29, please delete "SanBrook" and replace with -- Sambrook --.
Line 45, please delete "AND" and replace with -- and --.

Column 11,
Line 10, please delete "T4 Dna" and replace with -- T4 DNA --.

Signed and Sealed this

Seventh Day of May, 2002

Attest:

JAMES E. ROGAN
*Attesting Officer*     *Director of the United States Patent and Trademark Office*